US012622615B2

(12) United States Patent (10) Patent No.: US 12,622,615 B2
Roxhed et al. (45) Date of Patent: May 12, 2026

(54) INTERSTITIAL FLUID SAMPLING DEVICE

(71) Applicants: BonSens AB, Lidingö (SE); Niclas Roxhed, Bromma (SE); Federico Ribet, Stockholm (SE)

(72) Inventors: Niclas Roxhed, Bromma (SE); Federico Ribet, Stockholm (SE); Göran Stemme, Lidingö (SE)

(73) Assignee: BonSens AB, Lidingö (SE)

( * ) Notice: Subject to any disclaimer, the term of this patent is extended or adjusted under 35 U.S.C. 154(b) by 810 days.

(21) Appl. No.: 17/794,671

(22) PCT Filed: Jan. 22, 2021

(86) PCT No.: PCT/EP2021/051516
§ 371 (c)(1),
(2) Date: Jul. 22, 2022

(87) PCT Pub. No.: WO2021/148644
PCT Pub. Date: Jul. 29, 2021

(65) Prior Publication Data
US 2023/0077165 A1 Mar. 9, 2023

(30) Foreign Application Priority Data
Jan. 23, 2020 (SE) .................................... 2030019-0

(51) Int. Cl.
*A61B 5/15* (2006.01)
*A61B 5/145* (2006.01)
*A61B 10/00* (2006.01)
(52) U.S. Cl.
CPC .... *A61B 5/150022* (2013.01); *A61B 5/14514* (2013.01); *A61B 5/150763* (2013.01); *A61B 2010/008* (2013.01)

(58) Field of Classification Search
CPC .......... A61B 5/14514; A61B 5/150984; A61B 5/150977; A61B 5/150022;
(Continued)

(56) References Cited

U.S. PATENT DOCUMENTS 8,945,023 B2 * 2/2015 Mondro ............. G01N 27/3271
600/583
2007/0038148 A1 * 2/2007 Mechelke ........ A61B 5/150389
600/583
(Continued)

FOREIGN PATENT DOCUMENTS

EP 1187653 A2 3/2002
WO WO-0074763 A2 12/2000
WO WO-2019/126735 A1 6/2019

OTHER PUBLICATIONS

International Search Report and Written Opinion for PCT/EP2021/051516 filed Jan. 22, 2021 (published as WO 2021/148644 on Jul. 29, 2021) dated Apr. 7, 2021; 12 pages.

*Primary Examiner* — Daniel L Cerioni
*Assistant Examiner* — H.Q. Nguyen
(74) *Attorney, Agent, or Firm* — Harness, Dickey & Pierce, P.L.C.; Anthony G. Gussner

(57) ABSTRACT

A device for extracting an interstitial fluid sample from the skin of a mammal subject is disclosed. The device comprises at least one micro-needle comprising a tip portion configured to be inserted into the skin of the mammal subject, and a passage configured to transport the interstitial fluid from the skin to a retaining material arranged in a channel of a body of the device. The retaining material is fluidically connected to the passage and configured to absorb and store the interstitial fluid sample transported by the passage. A holder configured to receive such a device is also disclosed.

19 Claims, 4 Drawing Sheets

(58) Field of Classification Search
CPC ....... A61B 5/150412; A61B 2010/008; A61M
2025/0093; A61K 9/0021
See application file for complete search history.

(56) References Cited

U.S. PATENT DOCUMENTS

| | | | |
|---|---|---|---|
| 2007/0078358 A1* | 4/2007 | Escutia | A61B 5/150358 |
| | | | 600/583 |
| 2007/0083131 A1 | 4/2007 | Escutia et al. | |
| 2007/0161926 A1* | 7/2007 | Imamura | A61B 5/150503 |
| | | | 600/573 |
| 2009/0112125 A1* | 4/2009 | Tamir | A61B 5/150022 |
| | | | 600/583 |
| 2011/0125058 A1* | 5/2011 | Levinson | A61B 5/74 |
| | | | 600/584 |
| 2011/0144535 A1* | 6/2011 | Guirguis | A61B 5/157 |
| | | | 600/573 |
| 2015/0202418 A1 | 7/2015 | Simon et al. | |
| 2020/0315502 A1* | 10/2020 | Samant | A61B 10/0045 |
| 2022/0018736 A1* | 1/2022 | Tamir | A61B 5/145 |

* cited by examiner

INTERSTITIAL FLUID SAMPLING DEVICE

TECHNICAL FIELD

The present disclosure generally relates to the field of sampling of interstitial fluid, and in particular to techniques for extracting an interstitial fluid sample from the skin of a mammal subject.

BACKGROUND

To access information on the health of a patent beyond assessment of the symptoms, analyses of bodily samples need to be performed. Assessment of the concentration or presence of specific analytes in the body is an important aspect of medical practice for patient monitoring and disease diagnostics. Such an assessment allows for doctors and nurses to acquire information, either qualitative or quantitative, on the status of a patient and take medical decision based on thereon.

Depending on the disease or the condition to be assessed, different bodily matrices may be used, including tissue (for example via biopsy) and different fluids (both liquids and gases). Generally, it is common to use blood as a measurement matrix for a large variety of analytes, such as glucose, cholesterol, medical drugs, and the like. However, blood extraction is associated with invasive and painful methods, whether done via finger pricking or intravenously. Being able to monitor substances without the pain and discomfort associated with the blood sampling would therefore represent an improvement towards a more patient-centred healthcare. An emerging matrix for less invasive monitoring is the interstitial fluid (ISF), which has shown a good correlation with blood values for several analytes (such as glucose) and can be extracted from within the skin.

ISF is a liquid present between tissue cells of the body, outside the cells themselves and the blood vessels. The composition of the ISF is known to be rather similar to that of blood plasma. In addition to water it may comprise salts, glucose, small proteins, lipids, amino acids, fatty acids, hormones, neurotransmitter, and other small biomolecules. The similarity is understood to be due to a molecular exchange between the blood in capillary vessels and the interstitial space occurring by diffusion, hydrostatic pressure, osmotic pressure, active transporters, and transcytosis across the capillary endothelium. Because of this similarity with blood plasma, ISF is gaining a growing interest as a monitoring matrix.

Examples of current methods for ISF sampling involve the use of hollow microneedles that are inserted intradermally, and wherein an ISF flow is induced into the needles by vacuum suction. However, such techniques are relatively complex to use and associated with several drawbacks relating to e.g. incompatibility with current analytical standards in the clinics and difficulties ensuring a well-controlled and repeatable sampling volume.

Thus, there is a need for improved sampling techniques in general, and for an improved device for extracting ISF samples in particular.

SUMMARY

It would be advantageous to achieve a technique overcoming or alleviating at least some of the above-mentioned drawbacks. In particular it would be desirable to enable an improved device for extracting an ISF sample from the skin of a mammal subject.

To better address one or more of these concerns, a device and a holder having the features defined in the independent claims are provided. Preferable embodiments are defined in the dependent claims.

Hence, according to a first aspect, a device for extracting an ISF sample from the skin of a mammal subject is provided, comprising at least one micro-needle having a tip portion and a passage, wherein the tip portion is configured to be inserted into the skin of the mammal subject, and wherein the passage is configured to transport the ISF sample, extracted from the skin by the at least one micro-needle, away from the tip portion. The device further comprises a body configured to support the at least one micro-needle, and a retaining material arranged in a channel of the body. The retaining material is fluidically connected to the passage and configured to absorb and store the ISF sample transported by the passage.

According to a second aspect, a holder is provided, which is configured to receive a device according to the first aspect. The holder may also in some examples be referred to as a casing, a pressure generating means or an inserter. The holder comprises a rim portion configured to be placed on the skin and to at least partially encircle the at least one micro-needle when the at least one micro-needle is inserted in the skin. Further, the rim portion is configured to exert a pressure on portions of the skin adjacent to the at least one micro-needle to facilitate extraction of the ISF sample from the skin.

The above device and holder may further be used in a method in which the at least one micro-needle is inserted into the skin of the mammal subject and the ISF sample is extracted to the retaining material, in which the ISF sample is absorbed and stored. The extraction may be facilitated by the application of a pressure on portions of the skin adjacent to the at least one micro-needle, wherein the pressure may be applied by means of a rim portion of the holder.

The ISF sample, stored in the retaining material, may then be subject to biological or chemical analysis, e.g. performed by standard laboratory tools such as mass spectrometry. The chemical analysis may for example be performed to detect drugs of abuse, such as phosphatidylethanol, amphetamine, MFM, MDMA, tetrahydrocannabinol (THC), cocaine and opiates. The analysis may be performed for quantification purposes or for merely indicating presence of these substances.

The micro-needle may be understood as a micro-scaled needle which due to its small dimensions can be inserted into the skin relatively painlessly and without causing any significant tissue damage, especially as compared to conventional hypodermic needles. The device may comprise a plurality of micro-needles, for example arranged in two-dimensional arrays. The micro-needle may be formed from a variety of materials such as silicon or glass, metals such as stainless steel, or polymers such as for example a hydrophilic polymer. Preferably, the micro-needle has a length that allows its tip to be arranged in the dermis of the skin of the mammal subject. Hence, it is understood that the dimensions of the micro-needle may vary depending on the sampling location and the actual thickness of the skin at the sampling location. Various examples and dimensions of the micro-needle will be discussed later in connection with the description of different embodiments.

The micro-needle may hence be configured to penetrate the epidermis and provide access to the ISF in the dermal region. Due to its relatively small size, the use of the micro-needle may be relatively painless both during insertion and after removal, potentially improving patient acceptance and compliance. Further, by not drawing blood the risks of infections, which may be significant especially in point-of-care application, may be reduced. Moreover, the use of a micro-needle has shown to reduce the risk for long term damage to the skin, which makes it an attractive technique for repeated sampling compared to collecting venous blood or finger pricking.

The micro-needle may comprise a passage configured to transport the extracted sample from the tip towards the retaining material. The passage may be a hollow interior of the micro-needle, also referred to as a lumen, or a trench being arranged in an outer surface of the micro-needle and extending along the length direction of the micro-needle. In some examples, the passage may comprise a hydrophilic surface portion to enhance capillary action and facilitate extraction and transport of the ISF through the passage.

The retaining material may be provided to absorb and hold at least some of the ISF sample extracted by the micro-needle delivered to the retaining material via the passage. This allows for the sampled fluid to be stored within the device, or at least within the retaining material, so that it can be shipped to a laboratory in a stable from and be analysed. Storing the ISF sample in the retaining material thus simplifies the logistics normally required by blood or plasma transportation, which may involve refrigeration and is thus costly. Additionally, biohazards may be reduced by handling the retaining material instead of the sample in its liquid form. Advantageously, the present aspects allow for the characterisation chain used in dried blood spots sampling techniques to be involved for logistics and analysis. This allows for a relatively simple logistics and measurement in small (few microlitres) sample volumes, which combined with the relatively painless extractions from the patient may allow the ISF to be used as monitoring matrix for a broader number of medical applications in the clinics and for point-of-care sampling.

Examples of the retaining material, which also may be referred to as a capillary means or a capillary storing means, may is include analytical grade paper, such as dry blood spot paper.

A pressure gradient may be employed to facilitate the extraction of the ISF sample from the skin. This is due to the fact that ISF tends to be retained by the skin and, unlike blood, does not flow out spontaneously as there generally is no net hydrostatically induced pressure present in the ISF. Thus, to facilitate extraction of the ISF sample an external force may be applied to collect the ISF sample from the skin. The external force may for example originate from a mechanical pressure, a vacuum suction, or capillary forces. A pressure generating means may therefore be employed to overcome the physiological ISF retention by the skin and to reduce the sampling time. The rim portion disclosed in connection with the second aspect is an example of such a means, which may be configured to exert a mechanical force on portions of the skin adjacent or close to the tip of the micro-needle when inserted in the skin. The mechanical force may induce an overpressure in the tissue, driving the ISF towards the micro-needle.

The device may be releasably attached to the pressure generating means, thereby allowing the device to be removed after sampling and the pressure generating means to be reused for subsequent samplings. Alternatively, the pressure generating means is integrated in the device.

The micro-needle may be arranged to protrude from the body, preferably orthogonally, such that the top portion of the micro-needle is allowed to penetrate the skin in response to the body being placed on the skin. Thus, the ISF sample may be collected by arranging the body on the skin and pushing the device towards the skin such that the micro-needle is forced into the skin of the patient. Preferably, the micro-needle may be arranged on an underside of the body that is relatively flat so as to provide mechanical support during the extraction of the ISF sample. The underside of the body, i.e., the surface of the body adapted to be placed on the skin during the sampling, may comprise an adhesive for providing additional mechanical support and reducing the risk for unintentional movement of the device during the sampling. Advantageously, the adhesive may assist in stabilising the position of the micro-needle when pressure is applied to adjacent portions of the skin.

The retaining material may be arranged to at least partly intersect a fluidic passageway formed by the passage of the micro-needle. In other words, the retaining material may protrude into a hollow interior of the micro-needle, or into a trench arranged in a side of the micro-needle. In one example, the micro-needle may be provided with a groove or notch configured to allow the retaining material to directly contact the fluid transported in the passage. Further, the retaining material may be arranged to abut an end portion of the passage. Alternatively, or additionally, the passage may at least partly extend into the retaining material.

The above examples of the structural connection, or physical contact between the micro-needle and the retaining material, may advantageously serve the purpose of providing an efficient and reliable transport of the ISF fluid sample from the micro-needle into the retaining material, and reducing or minimizing the dead volume in the channel. In alternative examples there may however be a physical gap between the retaining material and the passage of the micro-needle, originating from the fact that the retaining material may be arranged at a distance from the passage of the micro-needle. The gap may for example be bridged by a portion of the channel in which the retaining material is arranged, allowing a fluidic connection by means of which the ISF sample can flow between the passage of the micro-needle and the retaining material even if there is no direct abutment between the retaining material and the passage of the micro-needle.

When the liquid front of the ISF sample has reached the retaining material, capillary forces of the retaining material may assist in the extraction of the remaining ISF sample from the skin and transport the ISF sample into the retaining material.

The retaining material may be understood as a material capable of absorbing and holding a liquid, such as ISF. The retaining material may be a porous material, which may be understood as a solid permeated by an interconnected network of pores or void. Preferably, the retaining material is hydrophilic so as to allow capillary filling and facilitate retention of the ISF sample. Examples of retaining materials include fibrous materials comprising cellulose (such as paper), glass fibres or polymeric fibres. The retaining material may be arranged to completely or at least partly fill the space forming the channel of the body. In one example, the retaining material may be provided as a sheet having a size that completely or at least partly covers a bottom surface of the channel.

The device may be provided with a fill level indicator to assist the user in determining when the predetermined amount or volume of ISF has been extracted and stored in the retaining material. This allows for the user to terminate the sampling at an appropriate time.

Several examples of fill level indicating mechanisms may be provided. In one example, a substance may be provided, configured to react with the ISF and change colour of the ISF sample. The substance may for example be provided in the retaining material, in which it may be mixed with the ISF as it progresses through the channel of the body. The change of colour may be into a colour that is relatively easy to detect for a user, for example through an inspection window arranged in a wall of the channel. This allows for the progress of the coloured ISF sample along the channel to be followed. The predetermined volume may for example be indicated by the coloured ISF sample reaching the window or a marking.

In another example, a metering capability, or fill level indication, may be provided by means of a functionalised line or region in the retaining material, configured to change colour upon wetting with the ISF.

Alternatively, or additionally, the fill level indicator may comprise a sensor or detector, which for example may be electrical or optical, configured to determine the fill level of the ISF sample in the retaining material. The sensor or detector may for example replace the optical inspection performed by the user as set out above. In an example, the fill level indication may be provided by means of an electrical resistance measurement configured to detect presence of ISF.

In a further example, time-control may be employed to determine or estimate the volume of the extracted ISF sample. Thus, the time during which the device is placed on the body and the tip of the needle inserted in the skin may be predetermined in order to control or at least affect the amount of ISF that is absorbed by the retention material.

The predetermined volume may in some examples be defined by the maximum volume the retention material is capable of receiving and storing. The maximum volume may in some examples be determined by the volume of the retention material. In case the retention material is a sheet-shaped material of a given thickness, the area of the sheet-sized material may be the factor defining the predetermined volume of the ISF sample. Thus, the volume metering of the sampled ISF may be determined by the geometrical dimensions of the retention material. Preferably, the predetermined volume may be 10 microlitres (μl) or less, such as for example 3 μl or less. In an example, the predetermined volume may be 1 μl or less. Such relatively small sample volumes (i.e. of a few microlitres) have the advantage that they may allow for a reduced sampling time.

The volume-metering, provided by the fill level mechanism and/or the predetermined filling volume of the retention material, advantageously allows for an improved quantitative analysis of the sample.

The tip portion of the micro-needle may have a radius of 50 micrometres (μm) or less, such as less than 5 μm or less. In an example, the radius is 1 μm or less. Further, the micro-needle may protrude 2000 μm or less from the body, such as 1000 μm or less. In an example, the micro-needle protrudes 500 μm or less. It will be appreciated that a reduced tip radius may be preferred in order to avoid or at least reduce the risk for damaging the tissue, and to reduce the risk for contaminating the ISF sample with blood. Further, it will be appreciated that the shape and in particular the length of the micro-needle may be selected to match the properties of the skin of the actual individual to be tested. Since the thickness of the skin, and the thickness and position of the dermis, may vary from individual to individual and also depend on the location on the subject's body, the micro-needle dimensions may be selected accordingly.

The passage of the micro-needle may be formed of a trench extending along at least a part of the micro-needle. In some examples, the passage may comprise a hydrophilic structure for facilitating transport of the ISF sample in the passage. The hydrophilic structure may for example comprise coating or layer increasing the hydrophilicity of the surface of the passage, and/or micropillars protruding from a surface of the passage. In a further example, the hydrophilic structure may comprise a porous material, preferably having a plurality of capillaries, absorbing the ISF sample and increasing the capillary action within the passage.

The pressure generating means, such as the holder, may comprise a resilient member configured to push the micro-needle towards the skin when the rim portion is placed on the skin. Advantageously, the resilient member is a spring, allowing the force by which the micro-needle is pushed against the skin to be determined by the spring constant of the resilient member rather than by the force by which the rim is pushed against the skin. Further, the pressure generating means may comprise an attachment means for securing the pressure generating means (and thus the micro-needle) to the skin and preferably push the rim of the pressure generating means against the skin to facilitate the extraction of the ISF sample. In case the locus is a forearm of the subject, the attachment means may be shaped as an armband.

Other objects, features and advantages of the enclosed embodiments will be apparent from the following detailed description, from the attached dependent claims as well as from the drawings. Those skilled in the art realise that different features of the present invention, even if recited in different claims, can be combined in embodiments other than those described above and in the following. For example, the holder according to the second aspect may form part of the device according to the first aspect. Similarly, the rim portion of the holder according to the second aspect, configured for exerting a driving overpressure guiding the ISF flow into the micro-needle, may form part of the device according to the first aspect. Further, it should be noted that the present disclosure is not necessarily limited to extraction of ISF samples from human patients. The device disclosed herein may as well be used for ISF sampling for veterinary purposes, even though it is appreciated that the dimensions of the micro-needle may be adjusted to suit the skin of the actual individual or species in question.

BRIEF DESCRIPTION OF DRAWINGS

Exemplifying embodiments will now be described in more detail with reference to the following appended drawings, on which.

As illustrated in the figures, the sizes of the elements and regions may be exaggerated for illustrative purposes and, thus, are provided to illustrate the general structure of the embodiments. Like reference numerals refer to like elements throughout.

DETAILED DESCRIPTION

Exemplifying embodiment will now be described more fully hereinafter with reference to the accompanying drawings, in which currently preferred embodiments are shown. The invention may, however, be embodied in many different forms and should not be construed as limited to the embodiments set forth herein; rather, these embodiments are provided for thoroughness and completeness, and fully convey the scope of the invention to the skilled person.

Figure 1:
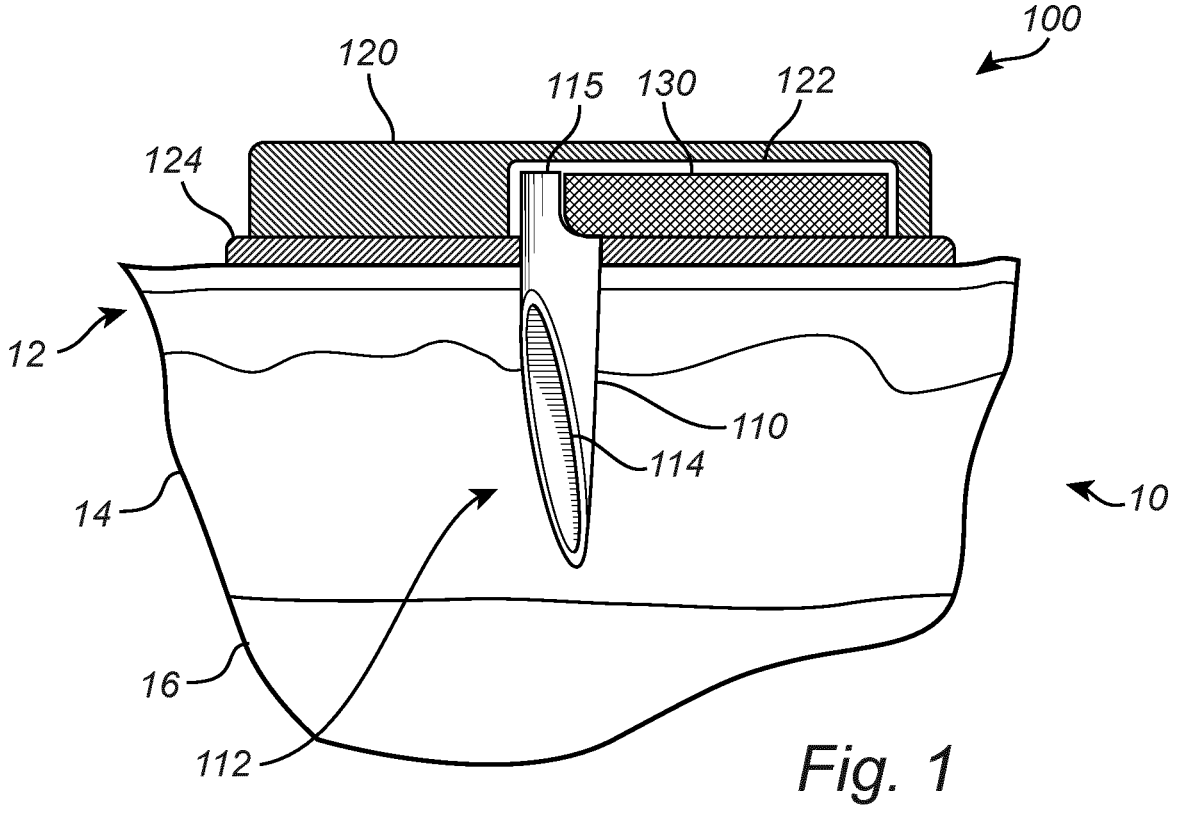
FIG. 1 is a cross section of a device according to an embodiment, when placed on the skin of the mammal subject.

FIG. 1 is a cross section of a device 100 according to an embodiment, comprising at least one micro-needle 110 comprising a tip portion 112 and a passage 114. The micro-needle 110 is supported by a body 120, comprising a retaining material 130 arranged in a channel 122 of the body 120. The retaining material 130 may be fluidically connected to the passage 114 and configured to absorb and store an interstitial fluid sample extracted from the skin 10 of a mammal subject. As indicated in the figure, the tip portion 112 is configured to be inserted into the skin 10 of the mammal subject, wherein the passage 114 is configured to transport the ISF sample, which is extracted by the micro-needle 110, away from the tip portion 112 and into the retaining material 130. Further, an adhesive (not shown) may be provided on an underside of the device 100, between the body 120 and the skin 10, for temporarily attaching or securing the device 100 to the skin 10 during the sampling. The adhesive may for example be a medical grade adhesive, preferably applied in a relatively thin layer of about 50 μm.

Generally, there are two main layers of the skin 10: epidermis 12 and dermis 14. Below dermis 14, a third layer of tissue is present; the hypodermis 16 (or subcutaneous tissue). The outermost layer, the epidermis 12, serves as a waterproof barrier enclosing the body of the subject and acts as a protection against infections. The middle layer, the dermis 14, protects the body from external stress and strain, and hosts thermo- and mechanoreceptors. The subcutaneous tissue 16 mainly consists of connective and fat tissue. Its main purposes are to attach the skin to muscles and bones, and to connect nerves and blood vessels to the skin 10. The thickness of the different layers strongly varies across different body locations and between different species, with the overall skin thickness of the human ranging from 0.05 millimetres on the eyelids to more than 1.5 millimetres on the feet soles. Considering the human forearm, the typical location used for example for blood sampling, the average skin thickness is about 1 millimetre.

ISF is a liquid present in all parts of the body between tissue cells, outside the cells themselves and the blood vessels. Because its similarity with blood plasma, ISF is gaining a growing interest as a monitoring matrix. In particular, skin ISF is very interesting for monitoring applications because of its accessibility. Moreover, the concentration of several bioanalytes is closely correlated to the one in blood, which is typically used as a medical standard. Substances such as glucose, for example, are present in approximately the same concentration as in blood, with just a short physiological delay, quantified in the order of 4 to 12 minutes, due to the diffusion time from the blood capillaries. Additionally, by targeting skin ISF, monitoring is not only potentially achieved in a minimally-invasive fashion, but continues monitoring with transdermal or intradermal devices can also be performed, providing a complete temporal picture of the evolution of the targeted analyte concentration.

Among the different skin compartments, the dermis 14 has shown to proportionally contain the largest amount and the most homogenously distributed ISF. Thus, the device 100 is preferably configured to allow the tip portion 112 of the micro-needle 110 to be arranged in the dermis 14 when the body 120 is placed on the skin 10 as illustrated in the present figure. However, the device 100 may also be configured to extract ISF from other parts of the skin 10, such as for example the hypodermis 16. The micro-needle 110 may for example protrude about 1 mm from the body 120 of the device 100, which has shown to be suitable for arranging the tip portion 112 in the dermis 14 of the forearm of a human. Further, the tip portion 112 may have a radius of curvature of about 5 μm to facilitate penetration of the skin. The micro-needle 110 according to the present example may be formed of stainless steel, which may reduce the cost compared to for example silicon-based microneedles and allow for standard manufacturing processes for needle cutting and shaping to be used. In the present example the micro-needle 110 is formed from a 32 G stainless steel needle processed by means of a femtosecond laser and cleaned in a 10% citric acid solution in DI water and sonicated, resulting in hydrophilic surfaces.

The end portion 115 opposite to the tip portion 112 may be arranged within the body 120, preferably in contact with the retaining material 130. The retaining material 130 may for example be arranged to overlap with a meniscus of ISF protruding from the end portion 115 of the micro-needle or be arranged to intersect the flow passageway formed by the lumen 114 of the micro-needle 110. In a further example, shown in for example FIG. 2 below, the end portion 115 of the micro-needle 110 may be inserted in the retaining material 130 such that the opening of the lumen 114 is arranged inside the retaining material. In the present example, as illustrated in FIG. 1, the end portion 115 of the micro-needle comprises a notch in which a portion of the retaining material 130 can be received to at least partly intersect the flow passageway formed by the lumen 114, thereby bridging the fluid flow. In the present example, the total length of the micro-needle is about 1.9 mm and the portion protruding from the body 120, preferably orthogonally from the lower surface of the body 120, about 1 millimetre.

The body 120, in which the micro-needle 110 and the retaining material 130 may be arranged, may be formed by for example a laminate of two or more layers. The body 120 may in an example comprise a base 124 of PMMA, on top of which two 170 μm thick layers of a double-adhesive tape and a plastic foil may be arranged, forming the channel 122 accommodating the retaining material 130. In other examples the body may be formed from silicon processing, moulding or 3D printing.

The retaining material 130 may be arranged to at least partly fill the channel 122 of the body 120. In the present example, the retaining material 130 is formed of a sheet of grade 238 paper that is processed to obtain a geometry able to store about 1 μl of liquid. An example of such a geometry will be discussed in connection with FIG. 4*a*.

During sampling, the base 124 of the body 120 may be arranged on the skin 10 of the mammal subject such that the tip portion 112 of the micro-needle penetrates the epidermis 12 and proceeds into the dermis 14. ISF of the skin 10 may then flow into the passage 114 of the micro-needle 110 and further into the retaining material 130 in the channel of the body 120, where the ISF sample may be stored. After the sampling, the device 100 can be removed from the skin 10 and stored for subsequent analysis.

The flow of ISF into the micro-needle may be facilitated or driven by capillary action of the passage 114 of the micro-needle and/or the retaining material 130, or by means of a pressure gradient generated by an applied mechanical pressure or a vacuum suction. An example of a technique employing an applied mechanical pressure will be discussed in the following with reference to the embodiment of FIG. 2.

Figure 2:
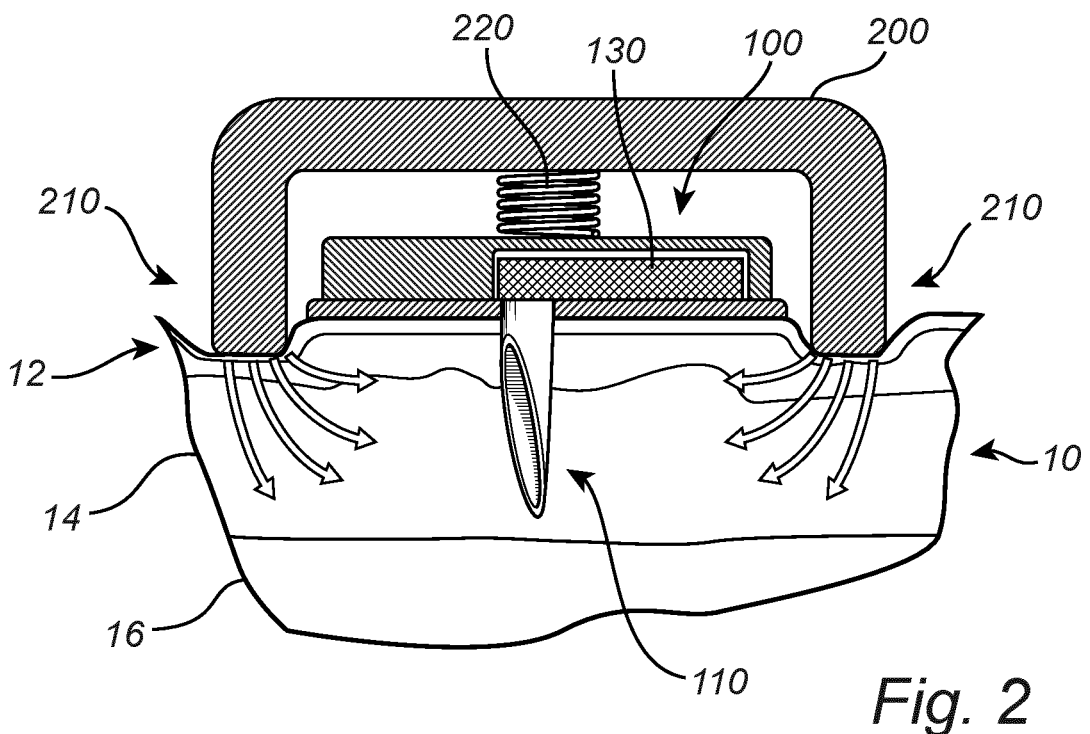
FIG. 2 is a cross section of a device when attached to a holder according to an embodiment.

FIG. 2 schematically illustrates the application of a mechanical pressure to the skin adjacent the micro-needle to facilitate extraction of the ISF sample. The mechanical pressure may be generated by a pressure generating means 200 configured to be placed on the skin 10 to exert a pressure on portions of the skin to drive ISF into the micro-needle 110. The pressure generating means 200 may for example comprise or be formed of a housing, or holder, having one or several a rim portions 210 adapted to be pushed against the skin 10 to generate a local, hydrostatic overpressure (indicated by arrows in the figure) in the ISF of the skin 10 during the sampling. While it is appreciated that the pressure generating means 200 may be structurally integrated in the device 100 as described above with reference to FIG. 1, FIG. 2 illustrates another example in which the pressure generating means 200 is a reusable inserter or holder and the device 100 is a disposable sampling device.

The pressure generating means 200 according to the present example may comprise a rim portion 210, which for example may be ring-shaped and at least partly encircle the micro-needle when placed on the skin 10. This allows for a pressure to be generated, which may converge radially towards the micro-needle to overcome the physiological ISF retention exercised by the skin. The rim portion 210 may form the open end of a casing or housing 200 configured to receive the sampling device 100 of FIG. 1. The sampling device 100 may be movable relative to the casing 200, allowing the rim portion 210 to exert a first force on the skin 10 and the sampling device 100 to exert second force on the skin, different from the first force. A resilient member, such as a spring element 220, may be arranged to keep the device 100 in the desired position in relation to the pressure generating means 200, or casing 200, and to allow for the micro-needle 110 to penetrate the skin 10. Further, the spring element 220 may be employed to push the sampling device 100 against the skin 10 during the sampling and thereby assist in keeping the device 100 in the desired position. The resilient member 220 may for example extend between an inner wall of the casing the and a top surface of the sampling device 100. The resilient member 220 may for example be formed as a helical spring or a flat spring, or any other flexible structures capable of resiliently guiding the sampling device 100 in a direction towards the skin 10 as the casing 200 is placed onto the skin 10.

It should be noted that the sampling device 100 may be similarly configured as the device 100 discussed in connection with FIG. 1. However, in the present example, the sampling device 100 differs from the device 100 of FIG. 1 in that the end portion 115 of the micro-needle 110 is inserted into the retaining material 130.

In further embodiments, however, a system is envisioned comprising three separate functional components: the device 100 as described above, a pressure generating means comprising a rim portion 210 as illustrated in for example FIG. 2, and an inserter for receiving and positioning the device 100. The inserter may be spring-loaded, comprising a resilient member 220 assisting in the positioning of the device 100 and, possibly, push the device 100 towards the skin 10 during the sampling. Preferably, the inserter is adapted to be reusable. The pressure generating means may in some examples be attached to the inserter. Further, the pressure generating means may be fixed to the inserter or moveable relative to the inserter.

Figure 3:
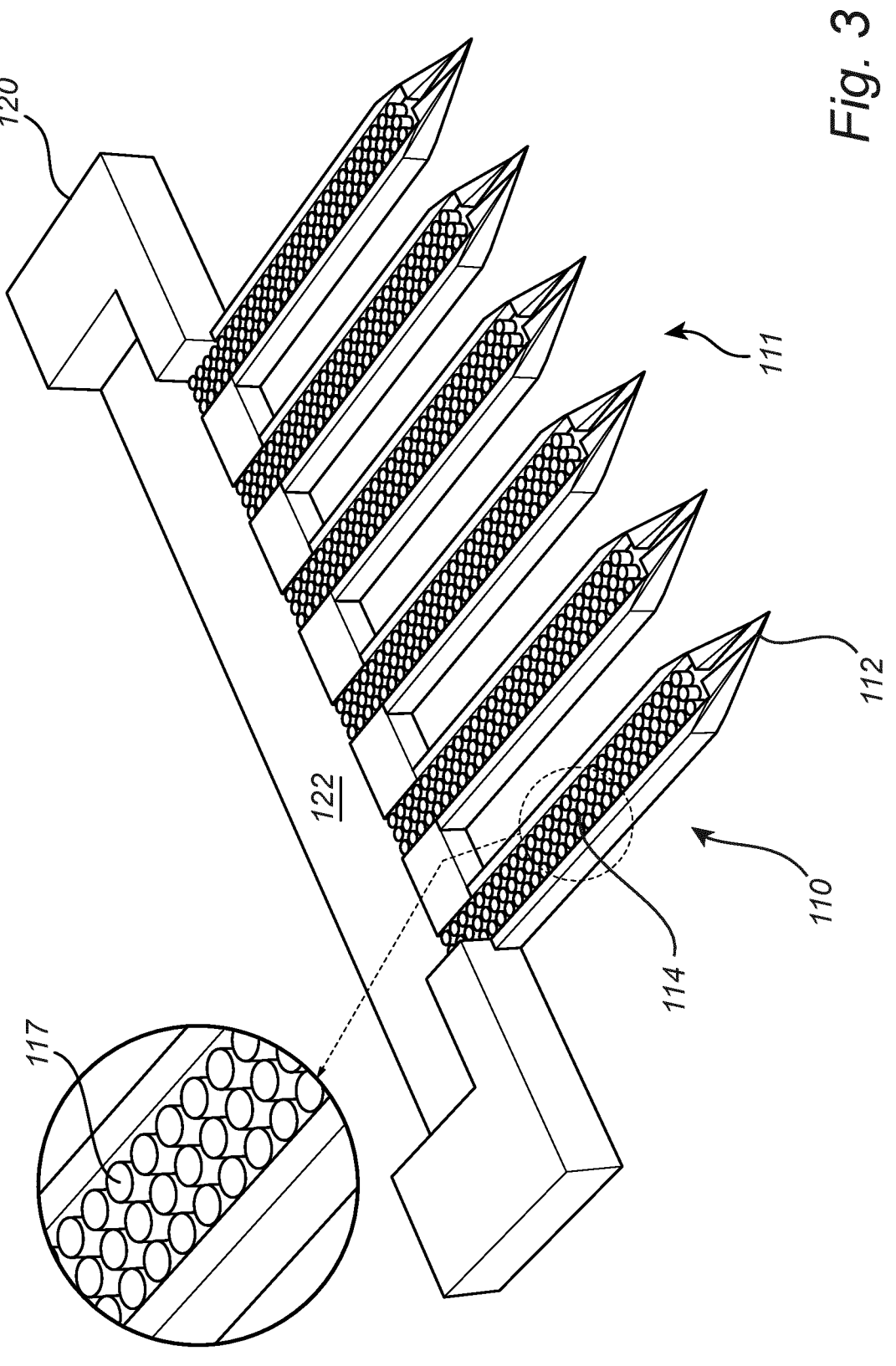
FIG. 3 is a perspective view of an array of micro-needles having a trench and a hydrophilic structure according to an embodiment.

FIG. 3 shows a portion of a device 100 which may be similarly configured as the devices 100 discussed in connection with FIGS. 1 and 2. The device of in FIG. 3 however differs in that it comprises more than one micro-needle, in the present example an array 111 of 7 micro-needles 110, formed from a semiconductor material such as for example silicon, using conventional semiconductor processing methods. The array 111 of micro-needles 110 may for example be arranged as an in-plane array 111 of the silicon substrate, with the micro-needles 114 extending in the main plane of extension of the silicon wafer substrate.

As indicated in the figure, the micro-needles 110 may be side-opened, i.e., having a passage 114 formed as a trench extending along a side of the micro-needle 110. The trench 114 may extend from the tip portion 112 of the micro-needle to the end portion 115 and fall into a channel 122 which may be common to all the micro-needles 110.

The channel 112 may comprise a structure 117 for increasing its hydrophilicity. In the present example, such a hydrophilic structure may be formed by a plurality of micropillars 117 protruding from an inner surface of the channel 112. The micropillars 117 may for example be formed when etching the channel 112 and may hence be arranged to protrude from a bottom surface of the channel (i.e., the surface opposing the open wall).

The device 100 may comprise one or several micro-needle arrays and is not limited to the array 111 and number of micro-needles 110 depicted in the present figure.

FIG. 4_a_ shows a cross sectional top view of a device 100 according to an example, which may be similarly configured as any of the devices 100 shown in FIGS. 1-3. The body 120 comprises a channel 122 that extends from the end portion 115 of the micro-needle to a fill level indicator 140, in the present example comprising a visualization window 142 and a marker 143. Further, the body 120 may comprise a vent hole 146 connected to the end of the channel for allowing air to escape the channel 122 as the liquid front 150 of the ISF sample progresses through the channel 122. The geometries of the channel 122, the window 142 and the vent hole 146 may be for example formed by laser cutting, using a carbon-dioxide laser, or by means of 3D printing, cutter plotting, or moulding.

The retaining material 130, such as for example a paper configured to absorb ISF, may be arranged in the channel 122 and provided with a shape that conforms with the channel 122. Thus, the amount of ISF that can be held by the paper, i.e., the maximum volume of the ISF sample, may be determined by the shape and size of the retaining material 130, also in case the channel 122 should have a shape differing from the shape of the retaining material 130. During operation, the ISF sample may be extracted by the micro-needle 110 and transported into the channel 122, where it is absorbed by the retention material 130. The progress of the absorption of the ISF sample may be indicated by the liquid front 150 spreading in the channel 122 and moving towards the vent hole 146 and the window 142, where it can be detected either manually by a user or by means of a sensor or detector as illustrated in FIG. 4_b_. In one example, the fill level indicator 140 may comprise a substance 145 configured to change a colour of the ISF sample. The substance may for example be a dry blue dye powder that has been added in a few micrograms to the retaining material 130 to be mixed with the ISF and to enable visualization of the front of the ISF flow during sampling.

The fill level indicator 140 may further comprise a marking 143 indicating a predetermined fill level, allowing for the user to stop the sampling by removing the device 100 from the skin 10 when the liquid front 150 has reached the marking 143. The marking 143 may for example be arranged such that it is visible through the window 142.

The geometry for the retaining material, such as a paper strip 130, may together with the fill level indicator 140 be used to ensure that the correct amount of ISF is absorbed before the sampling is stopped. Thus, by verifying that the liquid front 150 has reached the window 142 or marking 143 before the device 100 is removed from the skin 10, it can be assumed that a sufficient amount of ISF is present in the retaining material 130. To further improve quantification, a portion of the retaining material 130 can be used for the subsequent analysis. The portion may for example be selected to include the region closest to the micro-needle to ensure that at least that portion is completely filled with ISF. By selecting the size of the portion with high accuracy, a correspondingly high accuracy of the sample volume may be obtained.

Figure 4A:
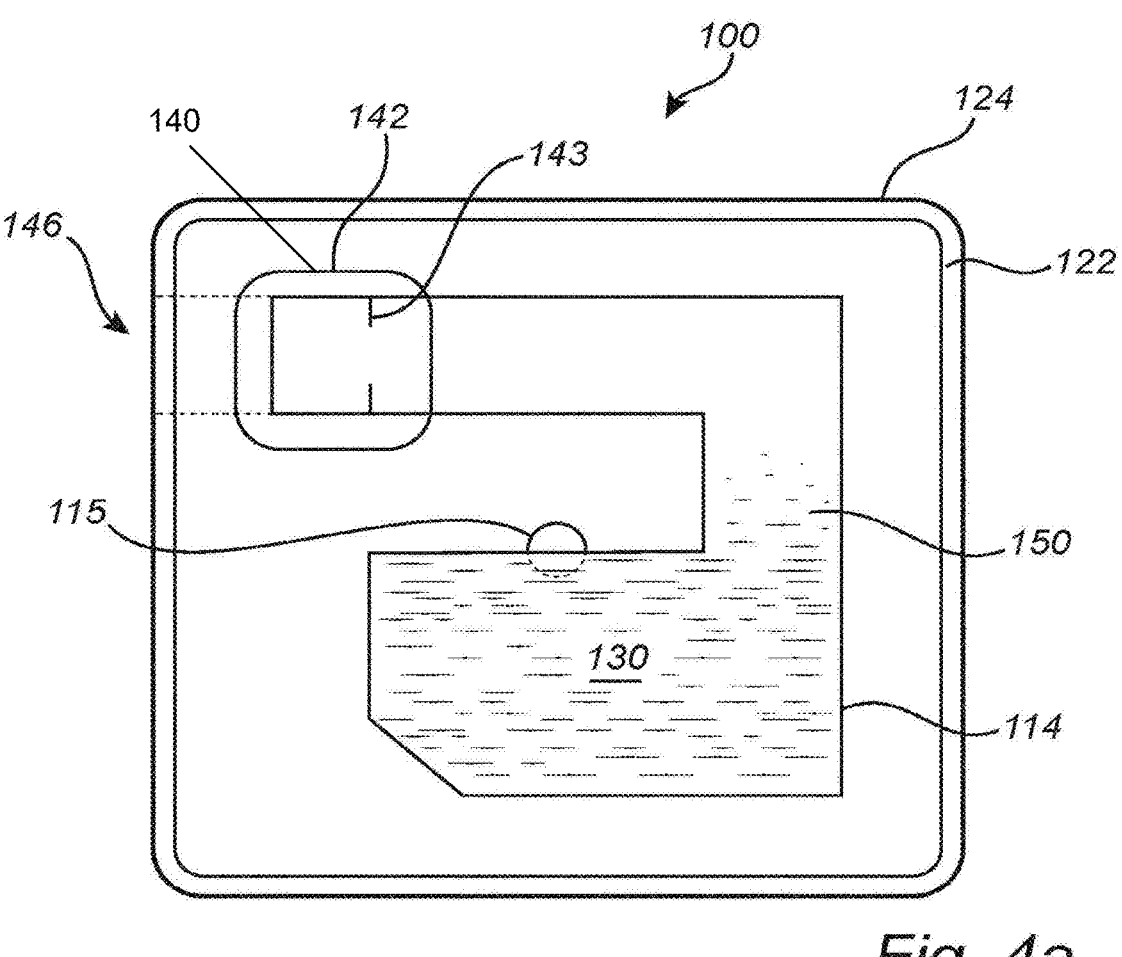
FIG. 4a is a top view of a device comprising a fill level indicator according to an embodiment.
Figure 4B:
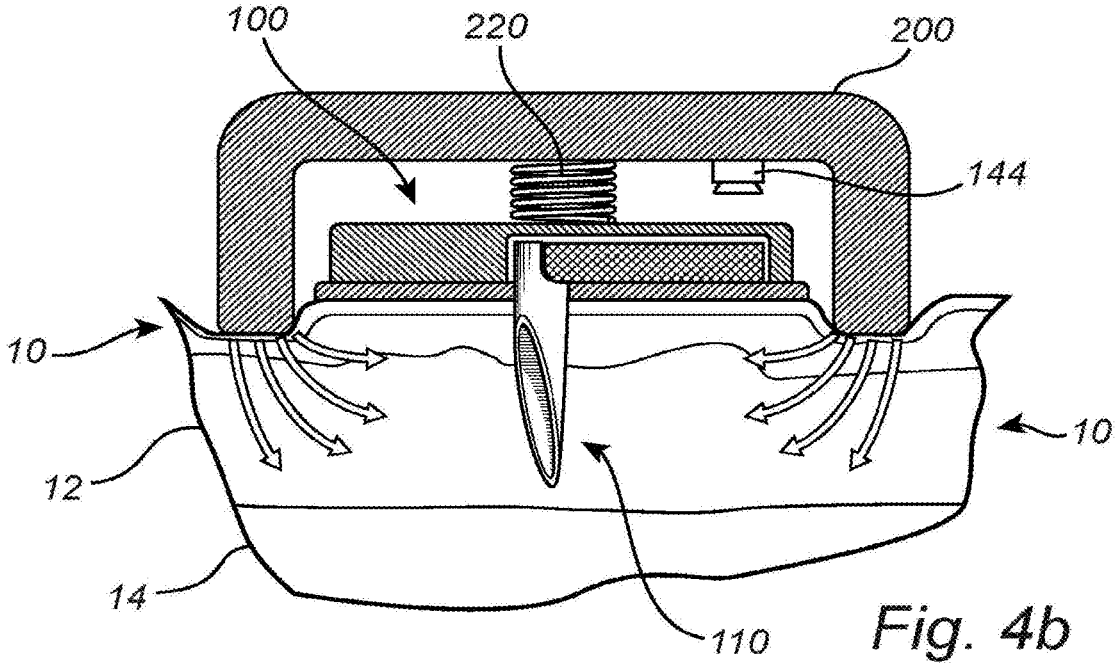
FIG. 4b is a cross section of a device comprising a fill level indicator according to another embodiment.

FIG. 4b shows a side view of the device of FIG. 4a when inserted in a holder 200 according to an example. The holder 200 may be similar to the one discussed above in connection with FIG. 2, which the addition of a sensor or detector 144 arranged to observe the fill level of the ISF sample in the retaining material 130. The sensor or detector 144 may for example be of an optical type, configured to monitor the window 142 and to output a signal carrying information indicating that the liquid front 150 has reached the window 142 or the marking 143.

Figure 5:
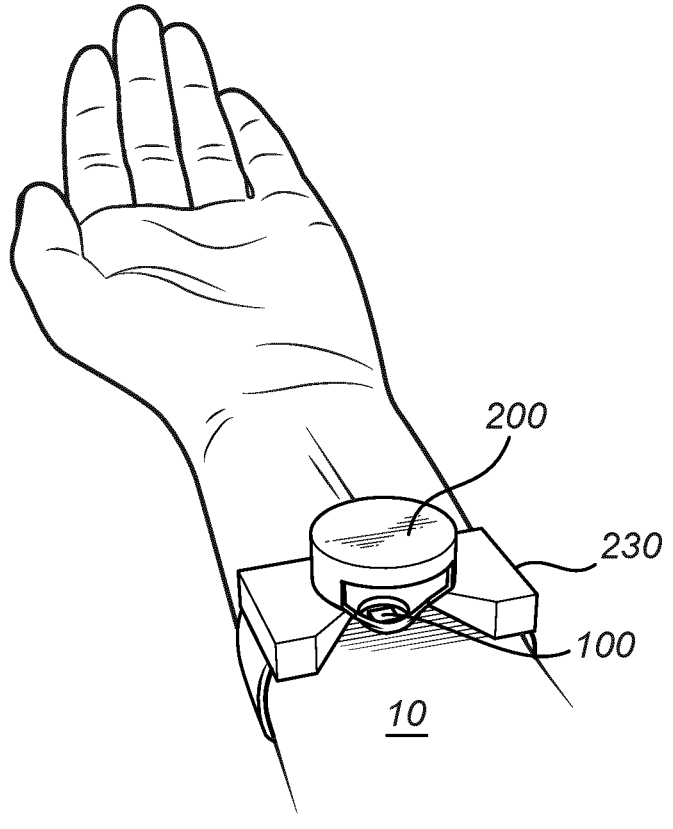
FIG. 5 is a perspective view of a device when placed on a forearm of a subject according to an embodiment.

FIG. 5 is a perspective view of a device 100, also referred to as a sampling chip 100, and a pressure generating means 200, which may be similarly configured as the devices 100 and pressure generating means 200 of the previous figures. Thus, the pressure generating means 200 may comprise a rim portion, such as a ring surrounding the sampling chip 100, forming part of a holder configured to releasably receive the sampling device 100. This allows for the sampling device 100 to be removed and the holder 200 to be reused. The holder 200 may be attached to the skin 10, such as for example the skin of an arm of a human, by means of an attachment means 230. The attachment means 230 may be shaped as an armband that can be tied to the arm.

Experimental Results

A device according to an embodiment of the present disclosure was evaluated in a study, which is recited in the following to further exemplify embodiments and possible use of the invention. The device was composed of two main parts: (i) the sampling device 100 similar to the ones described above, and (ii) an inserter, or holder 200, comprising a pressure generating means, or pressure ring, according to the above embodiments. The inserter was used for inserting the micro-needle in the skin and for the generation of a mechanical overpressure facilitating overcoming the physiological ISF retention by the skin to guide the ISF into the micro-needle lumen.

Volume-metering was provided by the geometry of the retaining material, in this example paper, and by a fill level indicator. In the present example the fill level indicator comprised coloured dye present in the paper itself. During sampling the liquid progressed within the paper matrix transporting the soluble coloured dye. Once the liquid reached the visualization window in the body, the device was removed from the skin.

The device, also referred to as a microfluidic chip, was designed to collect about 1 μl of ISF. The reliability was characterised in vitro. In most cases, sampling was completed within 5 minutes, with a variation between 3 and 8 minutes. The total number of samplings was in this study 15. The micro-needle insertion was reported as painless by all volunteers, in this case humans. The samples were analysed using liquid chromatography-tandem mass spectrometry (LC-MS/MS), with a similar protocol to the one developed for dried blood spots (DBS) analysis.

The metering accuracy was evaluated by pumping an artificial ISF solution (phosphate buffered saline solution, glucose, bovine serum albumin, dye) into the microneedle lumen at defined flow rates, which were varied between the different runs. At the time in which the liquid crossed the marking of the visualization window, the flow was stopped, and the total amount dispensed by the toll was recorded. For these tests, a syringe pump was used. The experiments were video recorded using a portable microscope camera.

To verify the possibility to measure relevant physiological concentration of analytes in small sample volumes by means of embodiments of the present invention, the concentration of caffeine in 1 μl spiked ISF surrogate was measured, as an example of a target molecule. The different concentrations in the various samples were successfully measured using LC-MS/MS, with protocols previously developed for analysis in whole blood from DBS paper.

For the presented measurements, 1 μl aliquots of dyed artificial ISF with the addition of caffeine at concentrations varying from 0.1 microgram per millilitre (μg/ml) to 9 μg/ml were pipetted into different paper pieces, in duplicates. Samples were then let dry into the paper matrix and stored. The dried samples were then evaluated and characterised using LC-MS/MS. Detection of caffeine was also confirmed in real ISF samples extracted from a human volunteer. Finally, to evaluate the penetration depth and the effect of microneedle penetration into the skin, an optical coherence tool was used.

The samples were collected on healthy human volunteers. The chosen sampling location was in the inner forearm, having a skin with layer thicknesses allowing access to the dermal region using 1 mm long microneedles. The sampling continued until the indicator was visualised by the operator unless the volunteer decided to interrupt the procedure earlier.

The volume-metering reliability of the used device was assessed by pumping an ISF surrogate solution into the device at known flow rates until it reached the visualisation window. The minimum and maximum flow rates used were 0.13 μl/min and 0.34 μl/min, respectively. These values correspond to the fastest and slowest sampling rates observed during in-vivo experiments. By imposing a flow rate of 0.13 μl/min, the indicator location was reached after dispensing 1.06 μl, while with 0.34 μl/min, 1.13 μl were dispensed. Therefore, the difference between the minimum and maximum flow rates was within +/−3.5%, with an average collected volume of about 1.1 μl.

The in-vivo sampling was performed by applying the device to the forearm. In this study, a spring-loaded inserter and a pressuring ring were used to achieve insertion and apply a radial force of about 10 N to lead dermal ISF to the micro-needle opening, respectively. The process was stopped when the liquid front reached the indicator location, in this example the edge of the visualisation window illustrated in FIG. 4a. The sampling time varied between 3 and 8 minutes (n=15) between different tests and individuals, with an average of 5 minutes.

The insertion speed and the micro-needle geometry may affect the skin penetration process due to the elastic properties of the skin. An OCT image of the needle inserted in the skin was acquired. The skin bending around the needle was approximately 150 µm. The needle opening, starting about 250 µm below the device base, was thus completely inserted inside the skin. One hour after the removal of the needle the pricking location could not be discerned using the OCT tool. The micro-needle insertion was reported as painless by all the individuals. Initially, signs of the skin pricking and the ring pressure were visible at and around the sampling location. The skin recovered within five hours. No permanent mark was visible days after the experiments.

The results of the experiments recited herein indicate that the embodiments of the present disclosure provide an efficient and minimally invasive technique for sampling ISF from mammal subjects. Compared to prior art techniques, the present device may be simpler, more compact and potentially more cost-effective due to the choice of materials, the fabrication techniques involved, and the lack of complex actuators. Further, the device may be disposable and possible to use with a reusable inserter or holder for facilitating extraction of the ISF sample from the skin.

The inventive concept has mainly been described above with reference to a few embodiments and examples. However, as is readily appreciated by a person skilled in the art, other embodiments than the ones disclosed above are equally possible within the scope of the inventive concept as defined by the appended claims.

The invention claimed is:

1. A device for extracting an interstitial fluid sample from the skin of a mammal subject, comprising:
  at least one micro-needle comprising a tip portion, an end portion with a notch, and a passage, wherein the tip portion is configured to be inserted into the skin of the mammal subject, and wherein the passage is configured to transport the interstitial fluid sample, extracted from the skin by the at least one micro-needle, away from the tip portion;
  a body configured to support the at least one micro-needle; and
  a retaining material arranged in a channel of the body; wherein the retaining material is fluidically connected to the passage and configured to absorb and store the interstitial fluid sample transported by the passage, and wherein the retaining material abuts the end portion of the at least one micro-needle by being received in the notch to at least partly overlap a liquid meniscus formed by the filling of the passage with the interstitial fluid sample.

2. The device according to claim 1, wherein the at least one micro-needle protrudes from the body such that the tip portion penetrates the skin in response to the body being placed on the skin.

3. The device according to claim 1, wherein the passage at least partly extends into the retaining material.

4. The device according to claim 1, wherein the retaining material is a porous material.

5. The device according to claim 1, wherein the device is configured to allow removal of the retaining material.

6. The device according to claim 1, further comprising a fill level indicator for indicating when the interstitial fluid sample stored in the retaining material reaches a predetermined volume.

7. The device according to claim 6, wherein the fill level indicator comprises a substance configured to change a colour of the interstitial fluid sample, and wherein the body comprises a window indicating a progress of the coloured interstitial fluid sample along the channel.

8. The device according to claim 6, wherein the fill level indicator comprises a sensor or detector configured to determine the fill level of the interstitial fluid sample in the retaining material.

9. The device according to claim 6, wherein the predetermined volume is 10 µl or less.

10. The device according to claim 1, wherein a tip radius of the tip portion is 50 µm or less, and wherein the micro-needle protrudes 2000 µm or less from the body.

11. The device according to claim 1, wherein the passage is formed by a trench extending along at least a part of the micro-needle.

12. The device according to claim 11, wherein the trench comprises a hydrophilic structure for facilitating capillary transport of the interstitial fluid sample.

13. A holder for a device for extracting an interstitial fluid sample from the skin of a mammal subject, the device including the structure of claim 1,
  wherein the holder comprises a rim portion configured to be placed on the skin and to at least partially encircle the at least one micro-needle when said at least one micro-needle is inserted in the skin, and
  wherein the rim portion is further configured to exert a pressure on portions of the skin adjacent to the at least one micro-needle to facilitate extraction of the interstitial fluid sample from the skin.

14. The holder according to claim 13, further comprising a resilient member configured to push the at least one micro-needle towards the skin when the rim portion is placed on the skin.

15. The holder according to claim 13, further comprising an attachment means for securing the holder to the skin.

16. A method for sampling an interstitial fluid sample from the skin of a mammal subject, the method comprising:
  inserting at least one micro-needle comprising a tip portion, an end portion with a notch, and a passage into the skin of the mammal subject,
  transporting the interstitial fluid sample through the passage away from the tip portion,
  absorbing and storing the interstitial fluid sample at a retaining material comprising a porous matrix, wherein the retaining material abuts the end portion of the at least one micro- needle by being received in the notch at least partly overlapping a liquid meniscus formed by the filling of the passage with the interstitial fluid sample, and
  analysing the interstitial fluid sample to measure or detect the presence of one or more analytes/markers.

17. A device for extracting an interstitial fluid sample from the skin of a mammal subject, comprising:
  at least one micro-needle comprising a tip portion and a passage, wherein the tip portion is configured to be inserted into the skin of the mammal subject, and wherein the passage is configured to transport the interstitial fluid sample, extracted from the skin by the at least one micro-needle, away from the tip portion;
  a body configured to support the at least one micro-needle;
  a retaining material arranged in a channel of the body; and
  a fill level indicator for indicating when the interstitial fluid sample stored in the retaining material reaches a predetermined volume;

wherein the retaining material is fluidically connected to the passage and configured to absorb and store the interstitial fluid sample transported by the passage, and wherein the retaining material abuts an end portion of the at least one micro-needle by being received in a notch of the end portion to at least partly overlap a liquid meniscus formed by the filling of the passage with the interstitial fluid sample.

18. The device according to claim 17, wherein the fill level indicator comprises a substance configured to change a colour of the interstitial fluid sample, and wherein the body comprises a window indicating a progress of the coloured interstitial fluid sample along the channel.

19. The device according to claim 17, wherein the fill level indicator comprises a sensor or detector configured to determine the fill level of the interstitial fluid sample in the retaining material.

\* \* \* \* \*